US009119949B2

(12) United States Patent
Brandl et al.

(10) Patent No.: US 9,119,949 B2
(45) Date of Patent: Sep. 1, 2015

(54) MEDICAL APPARATUS HAVING A SOCKET UNIT FOR CONNECTION OF A DEVICE FOR SUPPLYING MEDICAL FLUIDS, AND DEVICE FOR SUPPLYING MEDICAL FLUIDS HAVING A PLUG UNIT FOR CONNECTION TO A MEDICAL APPARATUS

(71) Applicants: Matthias Brandl, Bad Koenigshofen (DE); Thomas Faulhaber, Bergrheinfeld (DE); Joern Hoermann, Heusweiler (DE); Franz Kugelmann, St. Wendel/Bliesen (DE); Goekhan Oerter, Weilmuenster (DE); Rafael Sterzer, Schweinfurt (DE)

(72) Inventors: Matthias Brandl, Bad Koenigshofen (DE); Thomas Faulhaber, Bergrheinfeld (DE); Joern Hoermann, Heusweiler (DE); Franz Kugelmann, St. Wendel/Bliesen (DE); Goekhan Oerter, Weilmuenster (DE); Rafael Sterzer, Schweinfurt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 349 days.

(21) Appl. No.: 13/803,238

(22) Filed: Mar. 14, 2013

(65) Prior Publication Data
US 2013/0245530 A1      Sep. 19, 2013

Related U.S. Application Data

(60) Provisional application No. 61/611,605, filed on Mar. 16, 2012.

(30) Foreign Application Priority Data

Mar. 16, 2012   (DE) .......................... 10 2012 005 187

(51) Int. Cl.
*A61M 39/00*   (2006.01)
*A61M 39/10*   (2006.01)

(52) U.S. Cl.
CPC ......... *A61M 39/1011* (2013.01); *A61M 39/105* (2013.01); *A61M 2039/1027* (2013.01)

(58) Field of Classification Search
CPC .......... A61M 39/1011; A61M 39/105; A61M 2039/1016; A61M 2039/1027; A61M 2039/1033; A61M 2039/1066; F16L 37/12–37/138
See application file for complete search history.

(56) References Cited

U.S. PATENT DOCUMENTS

| 4,655,753 A | 4/1987 | Bellotti et al. |
| 7,984,928 B2 * | 7/2011 | Bergling et al. ................... 285/1 |
| 2007/0225673 A1 * | 9/2007 | Brehm et al. ................. 604/408 |

FOREIGN PATENT DOCUMENTS

| EP | 0 197 553 A2 | 10/1986 |
| EP | 0 575 970 A2 | 12/1993 |

(Continued)

OTHER PUBLICATIONS

International Preliminary Report on Patentability and Written Opinion in International Application No. PCT/EP2013/000769, dated Sep. 16, 2014.

*Primary Examiner* — Philip R Wiest
*Assistant Examiner* — Benjamin Klein
(74) *Attorney, Agent, or Firm* — Kenyon & Kenyon LLP

(57) ABSTRACT

A medical apparatus includes a socket unit for connection to a plug unit belonging to a device for supplying medical fluids for a blood treatment apparatus, the medical apparatus being in particular an extra-corporeal blood treatment apparatus such for example as an extra-corporeal dialysis apparatus or an apparatus for peritoneal dialysis, or an apparatus for filling the device for supplying medical fluids. A device for supplying medical fluids for a blood treatment apparatus, which has a plug unit for connection to a socket unit of a medical apparatus, is also described. The socket unit and the plug unit are characterised in that a safe and secure fluid-tight connection can easily be made with the two units between the device for supplying medical fluids and, on the one hand, the blood treatment apparatus or, on the other hand, the apparatus for filling the device for supplying medical fluids.

16 Claims, 10 Drawing Sheets

(56) References Cited

FOREIGN PATENT DOCUMENTS

| EP | 2 130 565 A1 | 12/2009 |
| EP | 2 452 720 A1 | 5/2012 |
| WO | 2010/140687 A1 | 12/2010 |

* cited by examiner

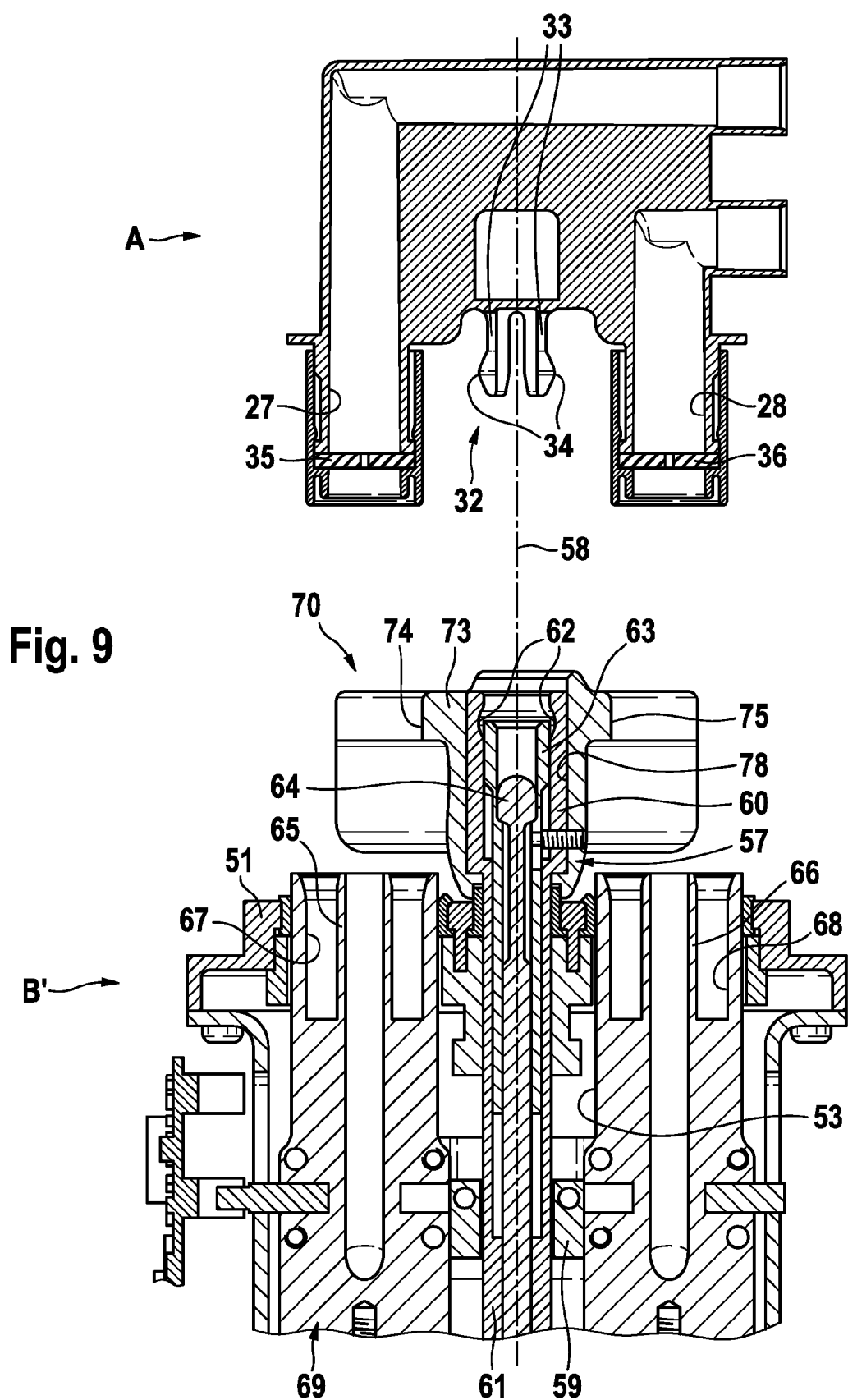

MEDICAL APPARATUS HAVING A SOCKET UNIT FOR CONNECTION OF A DEVICE FOR SUPPLYING MEDICAL FLUIDS, AND DEVICE FOR SUPPLYING MEDICAL FLUIDS HAVING A PLUG UNIT FOR CONNECTION TO A MEDICAL APPARATUS

CROSS REFERENCE TO RELATED APPLICATIONS

The present application claims priority to U.S. Provisional Application Ser. No. 61/611,605, filed on Mar. 16, 2012, and Application No. DE 10 2012 005 187.5, filed in the Federal Republic of Germany on Mar. 16, 2012, each of which is expressly incorporated herein in its entirety by reference thereto.

FIELD OF INVENTION

The present invention relates to a medical apparatus having a socket unit for connection to a plug unit belonging to a device for supplying medical fluids for a blood treatment apparatus, the medical apparatus being, in particular, an extra-corporeal blood treatment apparatus, such as for example an extra-corporeal dialysis apparatus or an apparatus for peritoneal dialysis, or an apparatus for filling the device for supplying medical fluids. As well as this, the present invention also relates to a device for supplying medical fluids having a plug unit for connection to a socket unit of a medical apparatus, and in particular of a blood treatment apparatus or an apparatus for filling the device for supplying medical fluids.

BACKGROUND INFORMATION

There are a large number of known connectors for connecting external components to units used in medical technology. The access to the units used in medical technology is generally gained by means of plugs which are inserted in mating sockets on the units used in medical technology. This being the case, the units used in medical technology, which will be referred to in what follows as items of medical apparatus, have a suitable socket unit while the external components have a plug unit.

What are used to treat patients suffering from kidney diseases are items of blood treatment apparatus which include in particular the known items of extra-corporeal blood treatment apparatus or items of apparatus for peritoneal dialysis. For the patient's blood to be cleansed, it is necessary for medical treatment fluids to be supplied. These include for example dialysis fluid or substitution fluid. In what is known as automatic peritoneal dialysis (APD) or acute dialysis, the medical treatment fluids are processed automatically in the medical blood treatment apparatus. The treatment fluids are supplied in fluid reservoirs which are connected to the treatment apparatus. The fresh dialysis fluid is pumped from the fluid reservoir into the blood treatment apparatus and used fluid is pumped out of the treatment apparatus and into the fluid reservoir. The fluid reservoir may already contain a concentrate which needs to be diluted with water. When this is the case, the fluid reservoir merely needs to be filled with water. Because of this, water too is understood to be a medical fluid in this connection. It is also possible for there to be a plurality of fluid reservoirs connected to a blood treatment apparatus when a treatment fluid ready for use is produced in the treatment apparatus by mixing a plurality of fluids. The liquid reservoir is once again connected to the blood treatment apparatus by a plug unit which is inserted in a socket unit on the blood treatment apparatus.

For filling the device for supplying dialysis fluid, there are known items of apparatus to which the devices for supplying dialysis fluid can be connected. For this purpose, the items of filling apparatus once again have a socket unit which can be connected to the plug unit of the device for supplying dialysis fluid.

A device for supplying a treatment fluid is described in, for example, European Application No. EP 0 575 970 A2. This device for supplying dialysis fluid comprises a bag for receiving the fluid, to which is connected a flexible line which is connected to a plug at its free end. The dialysis apparatus has a socket in which the plug is inserted. With the plug and socket, it is possible to make two flow-permitting connections to enable fresh dialysis fluid to be conveyed out of the bag and into the dialysis apparatus and used dialysis fluid to be conveyed back into the bag. To secure the plug against slipping out of the socket, the plug has latching noses which engage in recesses in the socket when the plug is fully inserted in the socket.

SUMMARY

The intention is for it to be as easy and safe as possible for medical personnel to connect the device for supplying medical fluids to the blood treatment apparatus or to the apparatus for filling the device for supplying medical fluids.

An object underlying the invention is to simplify for medical personnel the supply of medical fluids, and particularly dialysis fluid, to items of blood treatment apparatus, in particular extra-corporeal dialysis apparatus or apparatus for peritoneal dialysis and to increase the safety of the blood treatment.

The medical blood treatment apparatus according to the present invention or the apparatus according to the present invention for filling the device for supplying medical fluids has a socket unit, whereas the device according to the present invention for supplying medical fluids has a plug unit.

The socket unit and the plug unit are characterised in that a safe and secure connection can be made with the two units between the device for supplying medical fluids and, on the one hand, the blood treatment apparatus or, on the other hand, the apparatus for filling the device for supplying medical fluids.

To make the flow-permitting connection, the socket unit has at least one connecting piece, whereas the plug unit has at least one connector, a fluid-tight connection being able to be made when the connecting piece is connected to the connector.

In a preferred exemplary embodiment, the socket unit has a first connecting piece for connection to a first connector of the plug unit and a second connecting piece for connection to a second connector of the plug unit, thus enabling a first flow-permitting connection to be made for feeding in fresh treatment fluid and a second flow-permitting connection to be made for feeding out used treatment fluid.

It is immaterial to the basic principle of the present invention what form the connecting pieces and connectors take. The connecting pieces and connectors may, for their part, be plugs and sockets, respectively. The basic principle of the present invention lies in the socket unit having means by which either the at least one connecting piece of the socket unit is moved relative to the at least one connector of the plug unit or the at least one connector of the plug unit is moved relative to the at least one connecting piece of the socket unit.

This causes the connecting piece and connector to be connected automatically. There is therefore no need for the plug unit to be fully inserted in the socket unit. It is enough for the plug unit to be loosely inserted in the socket unit. The fluid-tight connection of the connecting piece and connector then takes place automatically.

The socket unit has means for connecting the plug unit and the socket unit which are so designed that, when the relative movement occurs between the at least one connecting piece of the socket unit and the at least one connector of the plug unit, the plug unit which at first was only loosely inserted in the socket unit is then firmly connected to the socket unit.

In a preferred exemplary embodiment, the connecting of the plug and socket units takes place simultaneously with the occurrence of the relative movement. It is however also possible for the plug and socket units to be connected together even before the connection of the connecting piece and connector takes place.

The present invention makes provision for two alternative exemplary embodiments, with one exemplary embodiment preferably being used in the blood treatment apparatus whereas the other exemplary embodiment is preferably used in the apparatus by which the device for supplying medical fluids is filled.

In the first alternative exemplary embodiment, the at least one connecting piece of the socket unit is arranged to be immovable on the socket unit, the means for moving the at least one connecting piece of the socket unit or the at least one connector of the plug unit being so designed that the plug unit is moved towards or away from the socket unit. In this exemplary embodiment, a relative movement thus takes place between the plug unit and the socket unit, the plug unit being automatically drawn into the socket unit to connect the connecting piece and connector.

In the first alternative exemplary embodiment the means for connecting the plug unit and the socket unit preferably have a receiving piece which is movable in the longitudinal direction and into which a complementary projecting piece of the plug unit can be inserted as a good fit. The means for moving the at least one connecting piece of the socket unit or the at least one connector of the plug unit preferably have an electric motor drive which moves the receiving piece. Rather than an electric motor drive, a pneumatic drive may equally well be provided.

A further preferred exemplary embodiment makes provision for the receiving piece of the socket unit to take the form of a tubular body displaceable in the longitudinal direction in which the projecting piece of the plug unit can be inserted.

In a further exemplary embodiment which is a particular preference, the receiving piece of the socket unit has recesses to receive latching noses on the projecting piece of the plug unit. A connection which latches in can be made in this way. However, the receiving piece and projecting piece are still not locked by this means.

To lock the projecting piece in the receiving piece, the means for connecting the plug unit and the socket unit preferably have a body in pin form which can be introduced into the projecting piece of the plug unit, the projecting piece of the plug unit thus being splayed apart to make a firm connection between the plug and socket units. The projecting piece of the plug unit is thus secured in the receiving piece of the socket unit to prevent it from slipping out. In this exemplary embodiment which is a particular preference, the locking of the projecting piece and receiving piece takes place by virtue of the fact that the splaying apart of the projecting piece secures the latching noses in the recesses to prevent them from slipping out.

The body in pin form for splaying the projecting piece of the plug unit apart is arranged in the socket unit preferably to be immobile and preferably in the tubular body of the receiving piece. This produces a compact structure.

A further exemplary embodiment of the present invention which is a particular preference makes provision for the projecting piece of the plug unit to be automatically detected in the receiving piece of the socket unit. The means for detecting the projecting piece in the receiving piece preferably have a sensing member which is resiliently pre-loaded and which is so arranged in the socket unit that, when the projecting piece of the plug unit is introduced into the receiving piece of the socket unit, the said sensing member is displaced in opposition to the resilient loading. The displacement of the sensing member can be detected by known means. What may be provided for this purpose are for example electrical contacts which are opened or closed when the sensing member is displaced, or a light barrier by which the position of the sensing member is detected.

In a further exemplary embodiment of the present invention which is a particular preference, the receiving piece, the tubular body and the body in pin form of the socket unit are concentrically arranged, thus producing a particularly compact structure.

Exemplary embodiments of the present invention will be described in detail with reference to the accompanying drawings.

BRIEF DESCRIPTION OF THE DRAWINGS

FIG. 9 is a view in section of the plug unit and socket unit shown in FIG. 7 before the said plug unit and socket unit are connected together.

DETAILED DESCRIPTION

Figure 1:
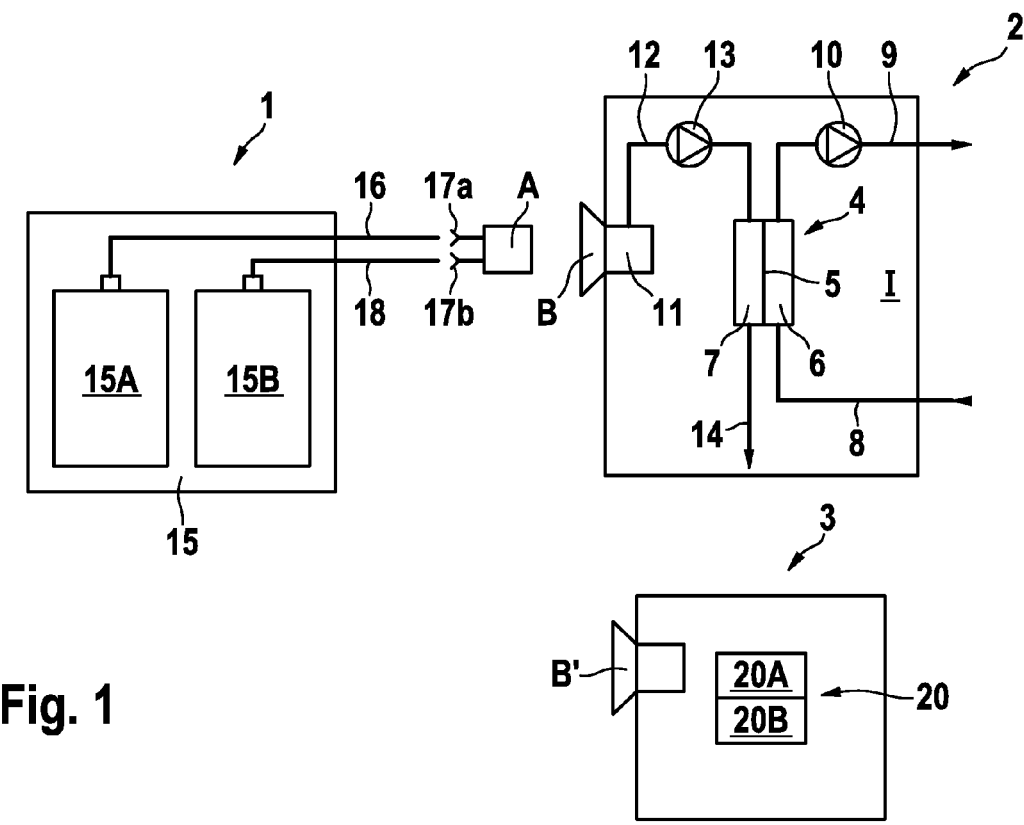
FIG. 1 is a highly simplified schematic view of a device for supplying a medical fluid, and particularly dialysis fluid, together with a blood treatment apparatus and an apparatus for filling the device for supplying dialysis fluid.

FIG. 1 is a highly simplified schematic view of a device 1 for supplying a medical fluid and in particular dialysis fluid, and of a blood treatment apparatus 2 and an apparatus 3 for filling the device for supplying dialysis fluid. The blood treatment apparatus 2 may be an extra-corporeal dialysis apparatus or an apparatus for peritoneal dialysis. In the present exemplary embodiment, the blood treatment apparatus 2 is a dialysis apparatus which has a dialyser 4 which is divided into a blood chamber 6 and a dialysis-fluid chamber 7 by a semipermeable membrane 5. A blood infeed line 8 runs from the patient to the blood chamber 6 of the dialyser 4 while a blood return line 9, into which a blood pump 10 is connected, runs from the blood chamber 6 to the patient. Together with the blood chamber 6, the blood infeed and return lines 8, 9 form the extra-corporeal blood circuit I of the dialysis apparatus 2.

Fresh dialysis fluid is conveyed from a dialysis-fluid reservoir 11, through a dialysis-fluid infeed line 12 into which a dialysis-fluid pump 13 is connected, to the dialysis-fluid chamber 7 of the dialyser 4, while used dialysis fluid flows out of the dialysis fluid-chamber through a dialysis-fluid outfeed line 14.

The device 1, which has two bags or canisters 15A and 15B in the present exemplary embodiment, is used to supply fresh dialysis fluid. The two bags or canisters 15A, 15B form a unit 15, the bag 15A being filled with fresh dialysis fluid before the dialysis treatment and the bag 15B being empty.

From the dialysis-fluid bag 15A, an infeed line 16 runs to one connection 17a of a plug unit A, while an outfeed line 18 runs from the other connection 17b of the plug unit A to the empty bag 15B.

To supply the dialysis fluid, the plug unit A is connected before the treatment to a socket unit B which is provided on the blood treatment apparatus 2, thus enabling fresh dialysis fluid to be fed through the infeed line 16 to the dialysis-fluid reservoir 10 and used dialysis fluid to be fed out through the outfeed line 18.

The device 1 for supplying dialysis fluid is filled with fresh dialysis fluid on the apparatus 3. The device 2 for supplying dialysis fluid can also be emptied by the filling apparatus 3. A tank 20A is used to hold fresh dialysis fluid and a tank 20B to receive used dialysis fluid. The lines and pumps required are not shown in the highly schematic representation.

The apparatus 3 for filling and emptying the device 1 for supplying fresh dialysis fluid and for receiving used dialysis fluid has a socket unit B' to which the plug unit A of the device 1 for supplying dialysis fluid is connected. The socket unit B of the blood treatment apparatus 2 and the socket unit B' of the filling or emptying apparatus may be of identical or different forms. In the present exemplary embodiment the socket units B and B' are of different forms. However, both the socket units B and B' are so designed that fluid-tight flow-permitting connections in both directions for fresh and used dialysis fluid can be made to the two items of apparatus 2 and 3 with the plug unit A of the device for supplying dialysis fluid.

Figure 2:
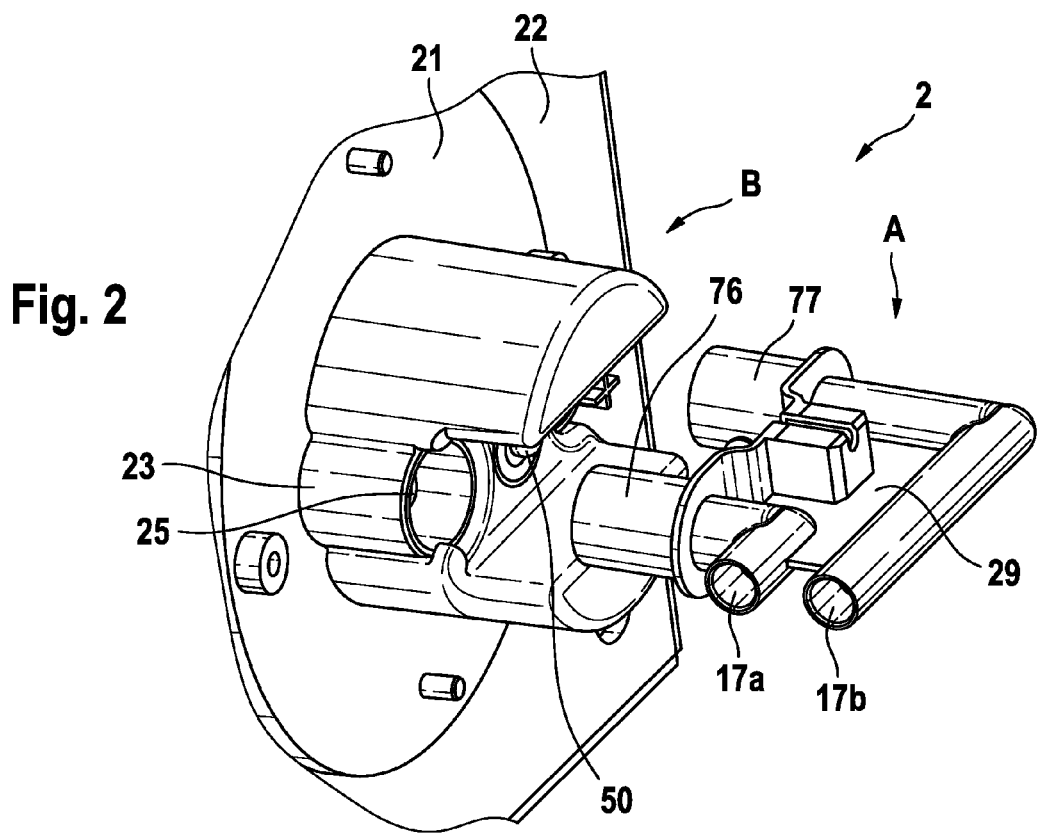
FIG. 2 is a perspective view of the plug unit of the device for supplying dialysis fluid and of the socket unit of the blood treatment apparatus shown in FIG. 1.

In what follows, the plug unit A of the device 1 for supplying dialysis fluid will be described in detail by reference to FIGS. 2 to 6, together with the socket unit B of the blood treatment apparatus 2. FIG. 2 is a perspective view of the plug unit A and the socket unit B, while FIGS. 3 to 6 show the plug and socket units A, B in section. The socket unit B of the blood treatment apparatus 2 is preferably part of a treatment cassette (not shown) which is interchangeable. The socket unit B may however also be part of a non-interchangeable unit. The socket unit B has an outer flange portion 21 which is screwed to the housing wall 22 of the treatment cassette or blood treatment apparatus 2 by screws (not shown). Projecting from the outer flange portion 21 are two cylindrical connecting parts 23, 24 which are arranged in a common plane on the two sides of the central axis 58 of the socket unit. The cylindrical connecting parts 23, 24 concentrically surround respective connecting pieces 25 and 26, the connecting piece 25 being used to feed in fresh dialysis fluid and the connecting piece 26 to feed out used dialysis fluid.

The plug unit A of the device 1 for supplying fresh dialysis fluid and receiving used dialysis fluid has corresponding connectors 27, 28 which will be connected to the connecting pieces 25, 26 with a fluid-tight seal. The plug unit A has a plug body 29 which connects the two connectors 27, 28. The plug body 29 has an infeed passage 30 which is connected to one connector 27 and an outfeed passage 31 which is connected to the other connector 28. The infeed line 16 of the device 1 for supplying fresh dialysis fluid and receiving used dialysis fluid is connected to the connection 17a of the infeed passage 30 and its outfeed line 18 is connected to the connection 17b of the outfeed passage 31. Situated between the two connectors 27, 28 is a projecting piece 32 with which a connection which at first is only loose can be made between the plug unit A and the socket unit B. The projecting piece 32 has a plurality of latching members 33 which are arranged to be circumferentially distributed and which are integrally formed on one end of the plug body 29. Formed on the outer sides of the free ends of the latching members 33 are latching noses 34. To protect them against physical contact, the connectors 27 and 28 have sleeves 76 and 77 which are fitted onto and latch into the connectors 27, 28 of the plug body 29. The connectors 27, 28 are closed off by respective membranes 35, 36 which will be pierced by the connecting pieces 25, 26 of the socket unit.

Mounted in the centre of the flange portion 21 of the socket unit B is a cylindrical guiding piece 37 which extends through a hole 38 in the housing wall 22. Guided to be longitudinally displaceable in the guiding piece 37 is a tubular receiving piece 40 which has a front portion 41 and a rear portion 42. A drive unit 43 is provided to displace the tubular receiving piece 40 in the cylindrical guiding piece 37. In the present exemplary embodiment, the drive unit 43 is an electric motor driven spindle drive which has a linear motor 44 and a spindle 45, which latter is connected to the rear portion 42 of the receiving piece 40. The receiving piece 40 is thrust out of the guiding piece 37 and retracted into the guiding piece by the extension and withdrawal of the spindle 45.

Provided in the interior of the front end of the front portion 41 of the receiving piece 40 are a plurality of recesses 46 which are arranged to be circumferentially distributed and which are of a form such that the latching noses 34 on the latching members 33 of the projecting piece 32 on the plug unit A latch into the recesses 46 when the projecting piece 32 is inserted in the receiving piece 40, a process which will be described in detail below.

The socket unit B has means by which it is detected that the projecting piece 32 is inserted in the receiving piece 40. These means have a sensing member 47, in the form of a tubular body, which is guided to be longitudinally displaceable in the tubular receiving piece 40. The tubular sensing member 47 is pre-loaded by a spring 48 which is mounted in the rear portion 42 of the receiving piece 40. A limit to the movement of the sensing member 47 in the longitudinal direction is set by a stop member 49 which is merely indicated and which is guided in a slot (not visible in the present plane of section) which is provided in the receiving piece 40.

To detect the projecting piece 32 in the receiving piece 40, the socket unit B has means by which it is detected whether the front end of the sensing member 47 is flush with the front end of the receiving piece 40 (FIG. 3) or whether it has been pushed back into the receiving piece in opposition to the pre-loading from the spring 48. This is the case when the projecting piece 32 is inserted in the receiving piece 40.

The socket unit B also has a body 50 in pin form which is arranged in an immovable position, inside the tubular sensing member 47. The body 50 in pin form may for example by locked by a pin 39 which extends through slots (not shown in the plane of section) in the sensing member 47 and the receiving piece 40 and into the guiding piece 37.

Figure 3:
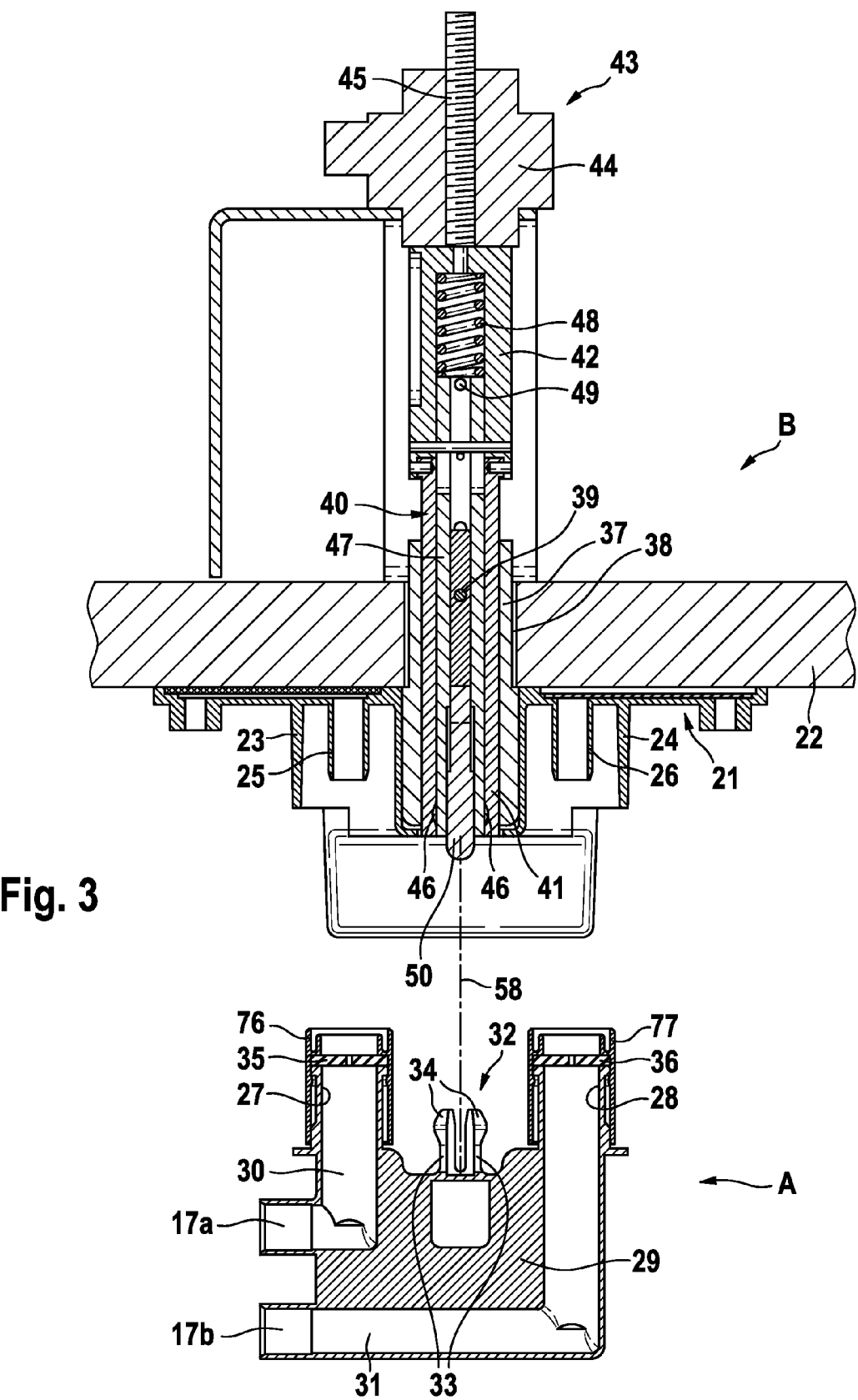
FIG. 3 is a view in section of the plug unit and socket unit shown in FIG. 2, in which the plug and socket units are not connected together.

In what follows, it will be described in detail how the plug unit A is connected to the socket unit B. FIG. 3 shows the starting position, in which the socket unit B is locked. In this position, the spindle 45 of the linear motor 43 is withdrawn, as a result of which the receiving piece 40 and the sensing member 47 are retracted and the body 50 in pin form thus projects from the receiving piece. The body 50 in pin form thus prevents the projecting piece 32 from being inserted in the receiving piece 40.

Figure 4:
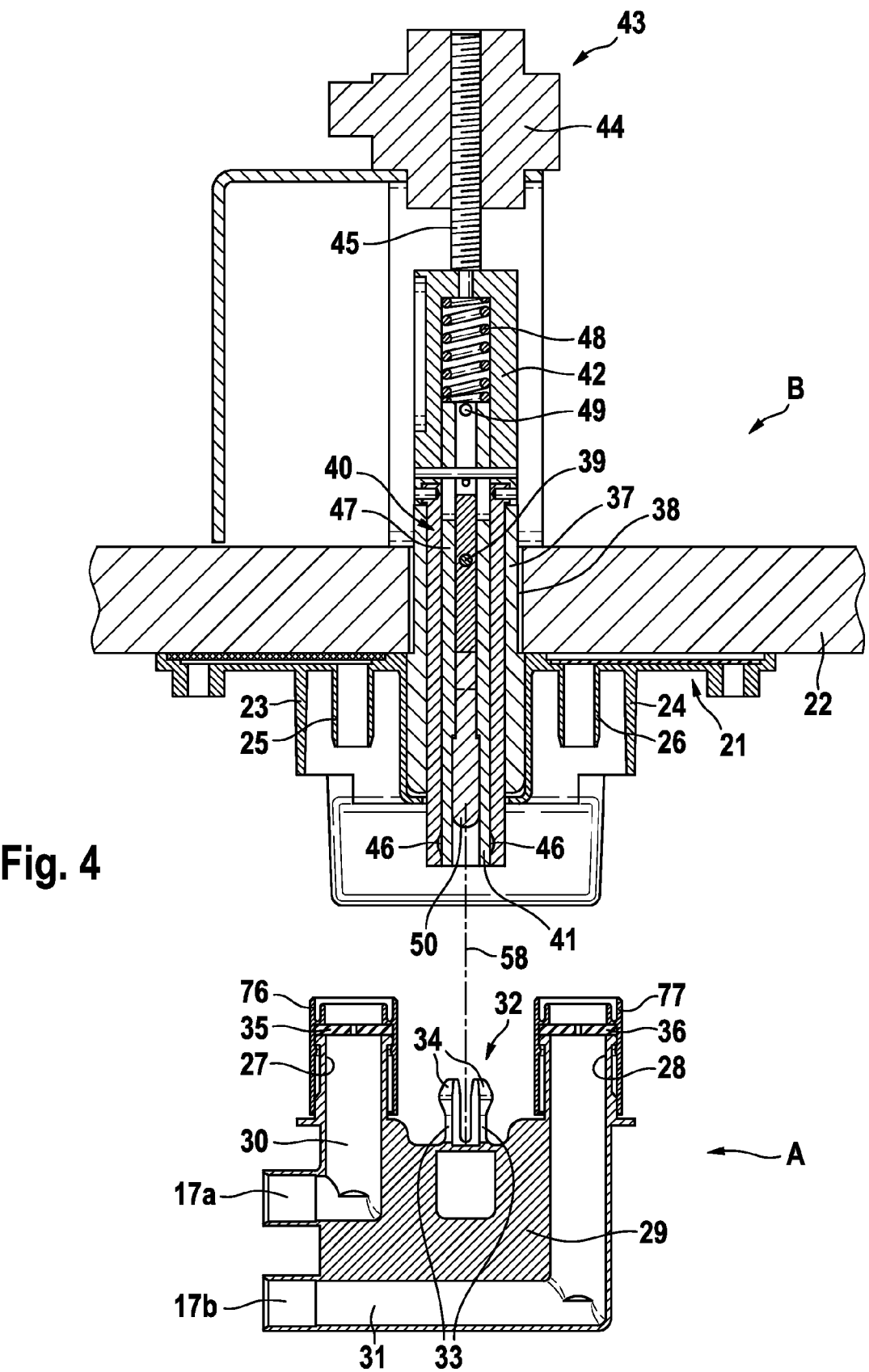
FIG. 4 is a view in section of the plug unit and socket unit shown in FIG. 2, in which the socket unit has been prepared to have the plug unit connected to it.

FIG. 4 shows the position of the receiving piece 40 and the sensing member 47 in which the spindle 45 of the linear motor 44 is extended and the receiving piece 40 and the sensing member 47 are advanced outwards out of the guiding piece 37. In this position the body 50 in pin form, which is connected to the guiding piece 37, is retracted sufficiently far for the projecting piece 32 on the plug unit A to be able to be inserted in the receiving piece 40.

Figure 5:
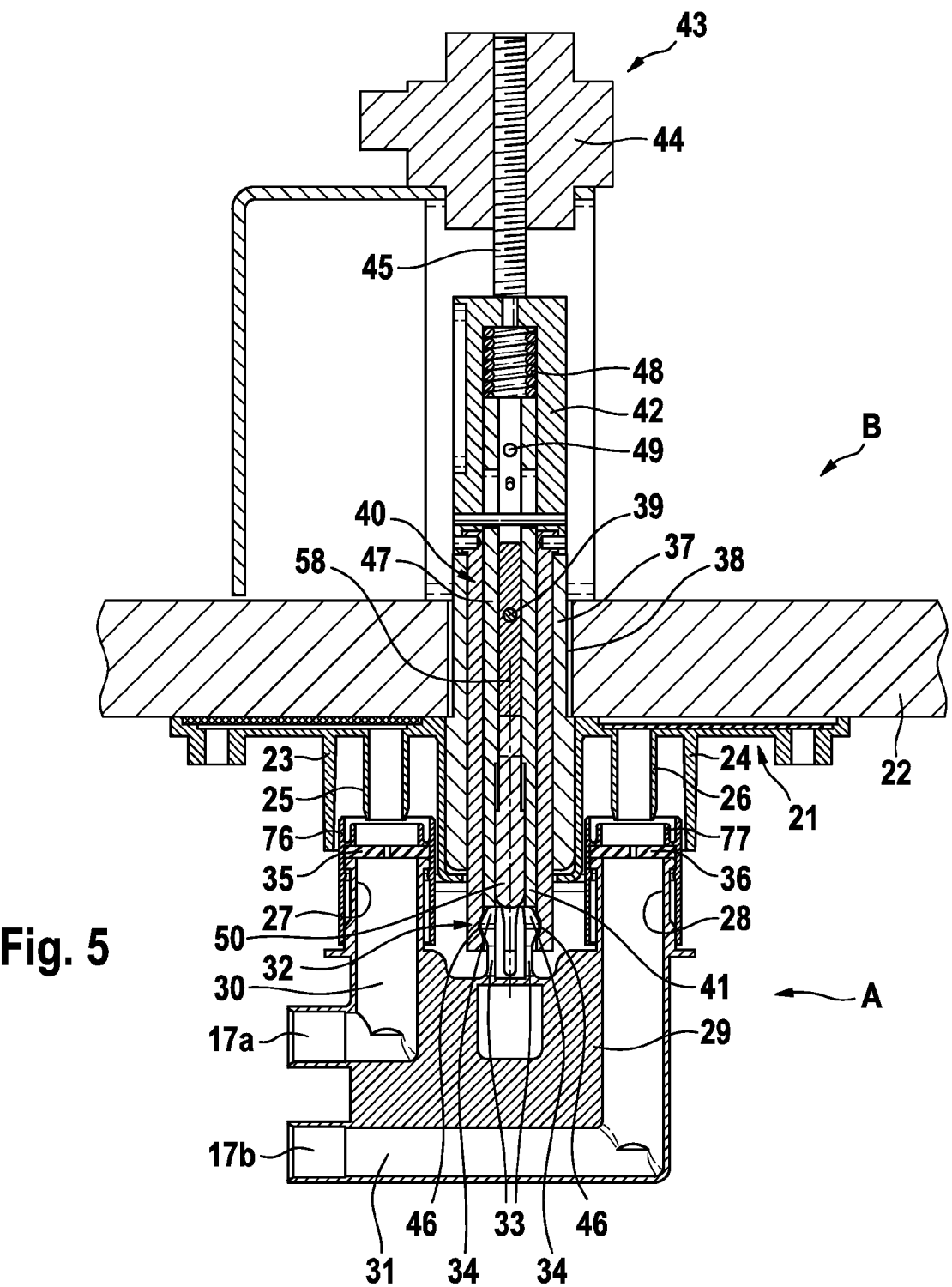
FIG. 5 is a section through the plug unit and socket unit shown in FIG. 2, in which the plug unit is loosely inserted in the socket unit.

FIG. 5 shows the projecting piece 32 on the plug unit A when fitted into the receiving piece 40 of the socket unit B. When the projecting piece 32 is inserted in the receiving piece 40, the latching noses 34 on the latching members 33 latch into the recesses 46 in the receiving piece 40 by a snap-in action. The plug unit A is held loosely to the socket unit by this means. However, the flow-permitting connection has not been made yet in this case, because the connecting parts 25, 26 of the socket unit B have not yet been connected to the connectors 27, 28 of the plug unit A. In this position the infeed and outfeed passages 30, 31 in the plug unit are still closed off with a fluid-tight seal by the membranes 35, 36.

When the projecting piece 32 is inserted in the receiving piece 40, the sensing member 47, which is guided to be longitudinally displaceable in the receiving piece, is pushed back into the receiving piece 40 by the latching members 33 of the projecting piece 32 in opposition to the resilient force of the spring 48. The withdrawn position of the sensing member 47, which is shown in FIG. 5, is sensed by means which are not shown, such for example as electrical contacts which are closed or a light barrier, as a result of which the drive unit 43 is started. The linear motor 44 now withdraws the spindle 45, and the receiving piece 40 and the sensing member 47 are thus retracted.

Figure 6:
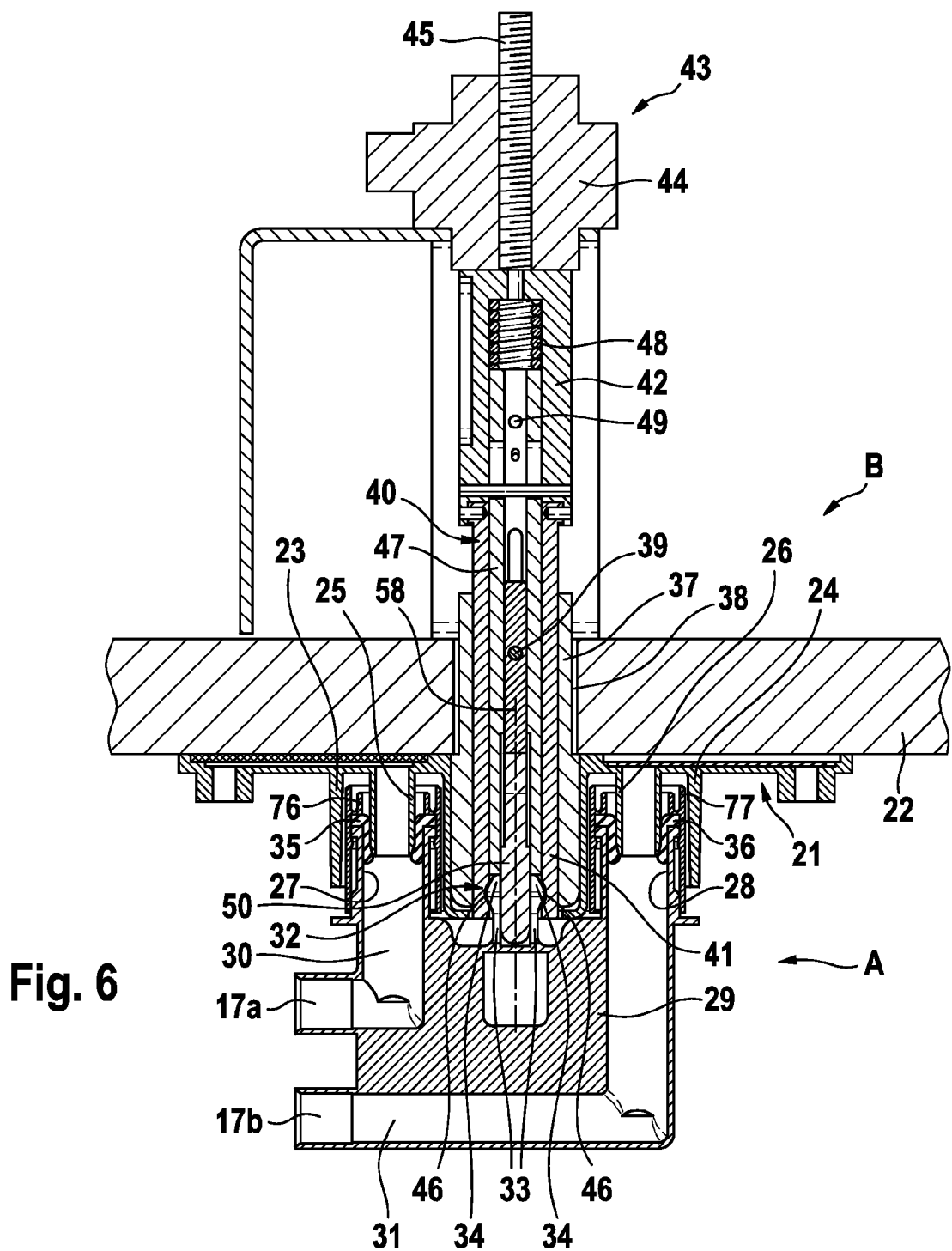
FIG. 6 is a section through the plug unit and socket unit shown in FIG. 2, in which the plug unit is connected to the socket unit, thus making the flow-permitting connections.

FIG. 6 shows the position of the receiving piece 40 when the spindle 45 of the linear motor 44 is completely withdrawn and the receiving piece 40 and the sensing member 47 are fully retracted. As the receiving piece 40 is retracted, the body 50 in pin form is advanced into the projecting piece 32, as a result of which the latching noses 34 on the latching members 33 of the projecting piece 32 are secured in the recesses 46 in the receiving piece 40. The projecting piece 32 is thus locked in the receiving piece 40. The locking of the projecting piece 32 in the receiving piece 40 takes place simultaneously with the relative movement of the connecting pieces 25, 26 and the connectors 27, 28.

In the position shown in FIG. 6, in which the spindle 45 of the linear motor 44 is fully withdrawn, the two connecting pieces 25, 26 and the two connectors 27, 28 are connected together with a fluid-tight seal. The locking of the projecting piece 32 in the receiving piece 40 on the one hand ensures that the plug unit A, which at first was only loosely inserted in the socket unit B, can be drawn onto the socket unit in opposition to the forces which arise, and on the other hand prevents the plug unit from being able to detach from the socket unit once the flow-permitting connections have been made. The fluid-tight and non-releasable connection between the plug unit A and socket unit B is thus made automatically once the plug unit has been loosely inserted in the socket unit.

The unlocking of the plug unit A from the socket unit B takes place in the reverse order from the locking of the plug unit to the socket unit. For this purpose, the drive unit 43 is started again. This may for example be done by pressing a button or the like. When the spindle 45 of the linear motor 44 is extended again, the receiving piece 40 and the sensing member 47 slide forward again over the body 50 in pin form, as a result of which the locking of the latched connection between the projecting piece 32 and receiving piece 40 is released. At the same time, the connecting pieces 25, 26 are disconnected from the connectors 27, 28. The plug unit A is thus situated in the starting position (FIG. 5) again, in which the plug unit is still held loosely on the socket unit. This prevents the plug unit from being able to drop easily off the socket unit.

FIGS. 7-11 show an alternative exemplary embodiment B' of the socket unit which is provided on the apparatus 3 for filling the device 1 for supplying the dialysis fluid. Basically, this alternative exemplary embodiment may equally well be provided on the treatment apparatus 2. It is however also possible for the exemplary embodiment which was described by reference to FIGS. 2 to 6 to be provided on the filling apparatus 3. The alternative exemplary embodiment B' of the socket unit will be described in detail in what follows.

Figure 7:
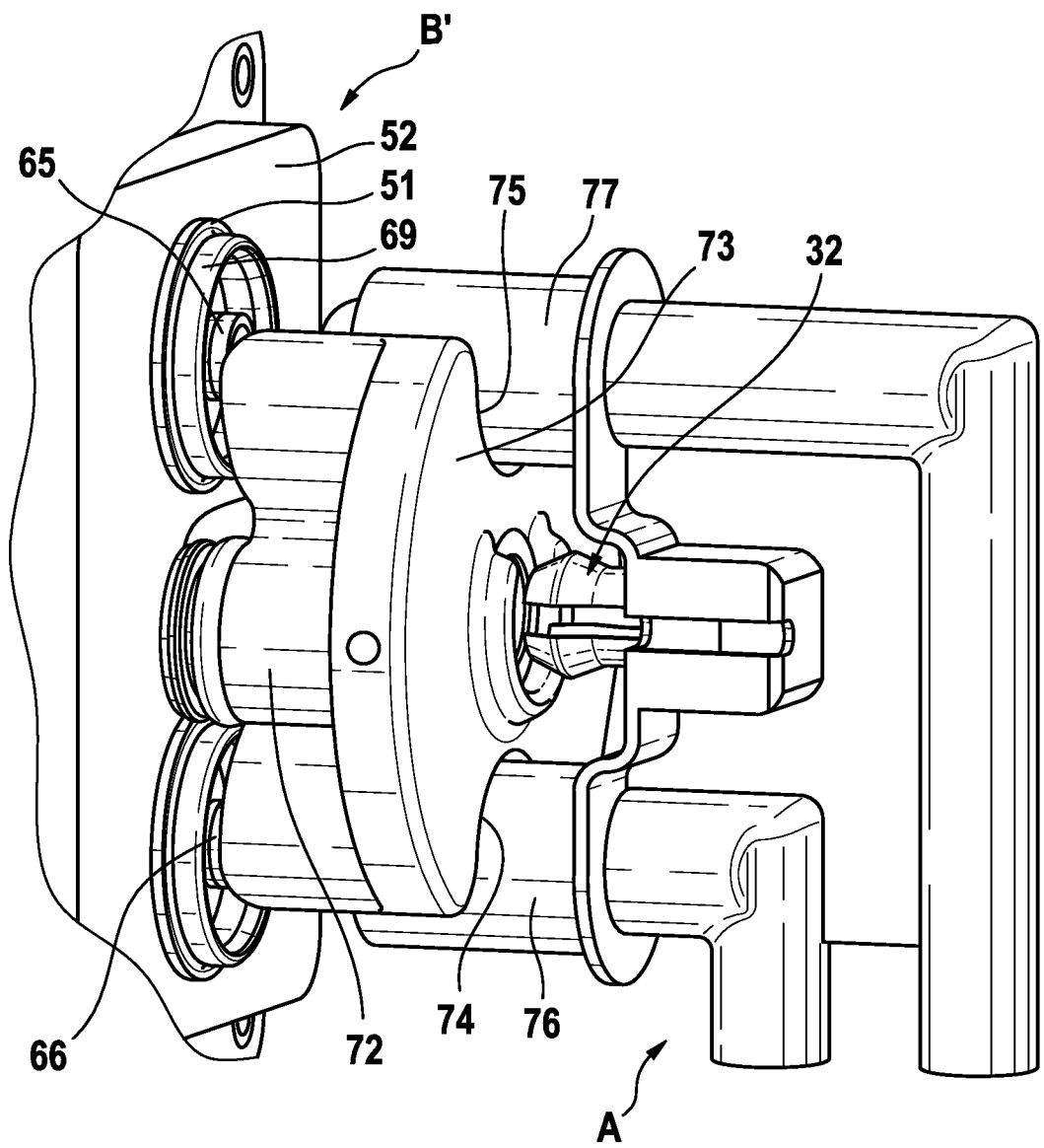
FIG. 7 is a perspective view of the plug unit of the device for supplying dialysis fluid and of the socket unit of the apparatus for filling the device for supplying dialysis fluid.

FIG. 7 is a perspective view of the alternative exemplary embodiment B' of the socket unit together with the plug unit A. Both the exemplary embodiments B and B' of the socket unit can be connected to the same plug unit A, thus enabling the device 1 for supplying dialysis fluid to be connected on the one hand to the apparatus 3 for filling and emptying and on the other hand to the blood treatment apparatus 2.

The two exemplary embodiments of the socket unit differ in particular in that, when the plug unit A is being connected to the socket unit B to make the flow-permitting connections, the connectors 27, 28 of the plug unit A are drawn automatically onto the connecting pieces 25, 26 of the socket unit B (FIGS. 2 to 6) by moving the plug unit A, whereas in the alternative exemplary embodiment B' of the socket unit the connecting pieces of the socket unit are moved into the connectors 27, 28 of the plug unit A, in which case the plug unit A is not moved. What is more, the alternative exemplary embodiment B' of the socket unit envisages the closing-off of the two connecting pieces or the making of a flow-permitting connection between the two connecting pieces for a flushing process without the plug unit A and socket unit B' being connected together.

The socket unit B' has a housing body 51 which is inserted in a wall 52 of the housing of the filling apparatus 3 (FIG. 7). The housing body 51 has a central opening 53 in which the receiving piece 57 for the projecting piece 32 of the plug unit A is arranged (FIG. 9). In contrast to the exemplary embodiment which was described by reference to FIGS. 2-6, the receiving piece 57 of the socket unit B' is not guided to be displaceable in the direction defined by the longitudinal axis 58 of the socket unit B' but is mounted to be rotatable on the longitudinal axis 58 by means of a bearing 59 which is inserted in the central opening 53 in the housing body 51. The receiving piece 57 is rotated by a drive unit which is not shown.

The receiving piece 57 has a front portion 60 which extends out of the housing body 51 and a rear portion 61 which extends into the housing body 51, the front portion 60 being of a larger inside and outside diameter than the rear portion 61. Provided on the inside of the front end of the front portion 60 of the receiving piece 57 are the recesses 62 which are arranged to be circumferentially distributed and into which the latching noses 34 on the latching members 33 of the projecting piece 32 latch when the plug unit A is fitted loosely onto the socket unit B'.

Guided to be longitudinally displaceable in the tubular receiving piece 57 is the sensing member 63, which takes the form of a tubular body and which is pre-loaded by a spring (not shown) so that the sensing member 63 is pushed back in opposition to the loading from the spring when the projecting piece 32 is inserted in the receiving piece 57.

Guided in the tubular sensing member 63 is the body 64 in pin form for locking the projecting piece 32 in the receiving piece 57. The body 64 in pin form can be advanced in the longitudinal direction of the axis 58 and retracted again, to respectively lock and release the projecting piece 32 in the receiving piece 57, by a drive unit (not shown).

In the alternative exemplary embodiment B' of the socket unit, the connecting pieces 65, 66 are mounted in cylindrical openings 67, 68 in a connecting part 69 which is guided to be longitudinally displaceable in the housing body 51, thus enabling the connecting pieces 65, 66 to be advanced out of and retracted into the housing body 51. The drive unit for advancing and retracting the connecting part 69 having the connecting pieces 65, 66 is not shown in the drawings.

FIG. 9 shows the socket unit B' in the position in which the plug unit A is fitted loosely onto the socket unit B'. The body 64 in pin form is retracted into the receiving piece 57 and the latching members 33 of the projecting piece 32 which have the latching noses 34 are thus able to latch into the receiving piece 57 which has the recesses 62.

Figure 10:
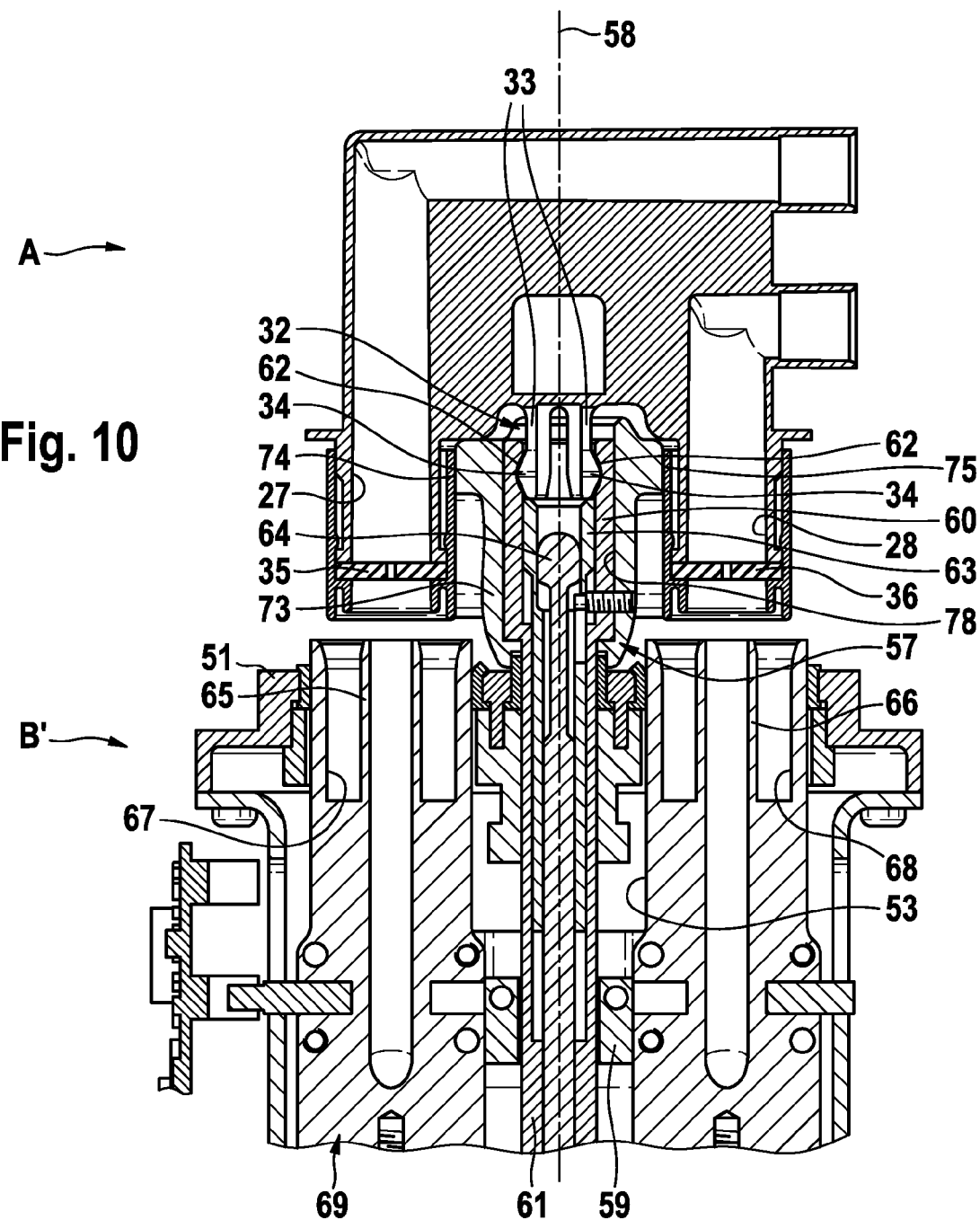
FIG. 10 is a view in section of the plug unit and socket unit shown in FIG. 7 in which the said plug unit is fitted loosely onto the said socket unit.
Figure 11:
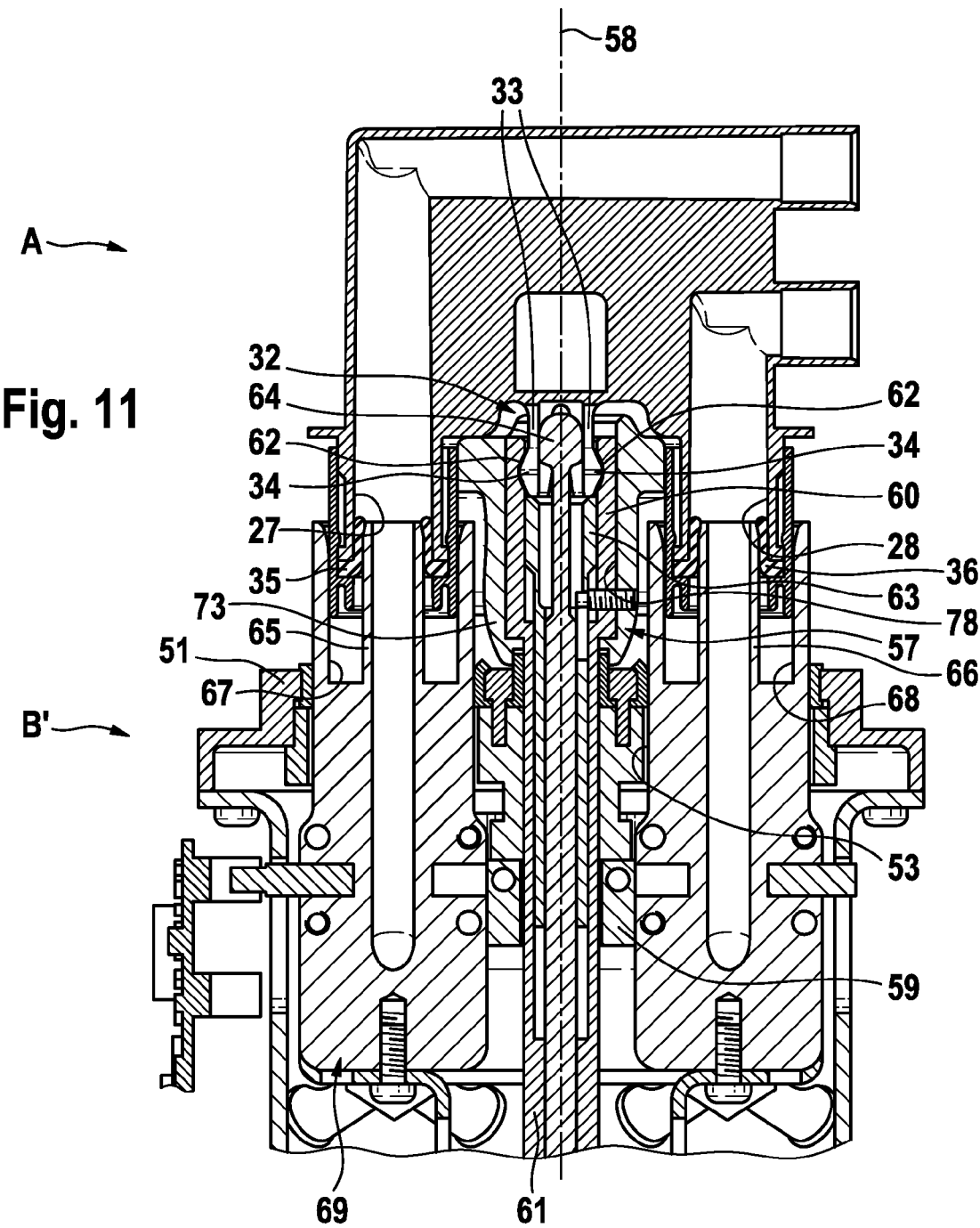
FIG. 11 is a view in section of the plug unit and socket unit shown in FIG. 7 in which the said plug unit and socket unit are connected together to make the flow-permitting connections.

FIG. 10 shows the position in which the plug unit A is fitted loosely onto the socket unit B', with the projecting piece 32 latched into the receiving piece 57. The plug unit A is held only loosely in this case without the flow-permitting connections being made.

The position of the sensing member 63 is once again monitored. Because the sensing member 63 has been pushed back by the projecting piece 32, it is detected that the plug unit A has been loosely fitted. When the plug unit is loosely fitted, the drive unit (not shown) is started, as a result of which the body 64 in pin form is advanced in the receiving piece 57. As a result, the connection between the projecting piece 32 and receiving piece 57, which at first was only loose, is now locked. At the same time, the connecting part 69 having the two connecting pieces 65, 66 is advanced out of the housing body 51. It is also possible for the body 64 in pin form and the connecting part 69 to be connected together and to be moved in unison by a drive unit. The displacement of the connecting part 69 and the two connecting pieces 65, 66 causes the connecting pieces 65, 66 to pierce the membranes 35, 36 of the plug unit A, as a result of which the fluid-tight connections are made between the connecting pieces and the connectors. It is true that there is, once again, a relative movement between the connecting pieces 65, 66 and the connectors 27, 28. However, in this exemplary embodiment it is not the plug unit A itself which is moved. Because the plug unit A is firmly seated on the socket unit B' once the projecting piece has been locked to the receiving piece, the forces which occur when the plug and socket units are connected together can be absorbed. The connection of the plug unit to the socket unit thus once again takes place automatically.

The release of the plug unit A from the socket unit B' takes place in the reverse order. For this purpose, the body 64 in pin form is retracted in the receiving piece 57 and the connecting part 69 and the connecting pieces 65, 66 are retracted in the housing body 51, as a result of which the connection between the projecting piece 32 and receiving piece 57 is unlocked and the connecting pieces 65, 66 are drawn out of the connectors 27, 28. The unlocking may take place simultaneously with the drawing back of the connecting pieces or prior to the said drawing back of the connecting pieces.

Figure 8A:
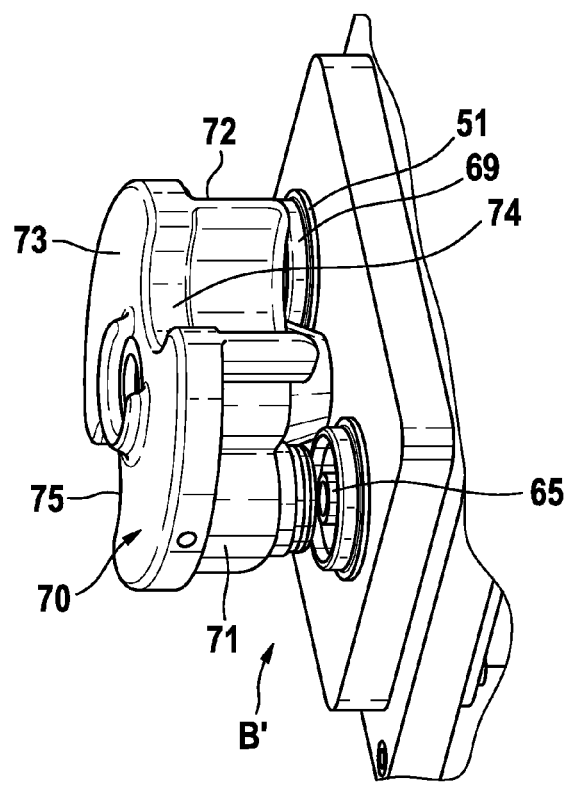
FIG. 8A shows the socket unit shown in FIG. 7 when prepared for the initiation of a flushing process.
Figure 8B:
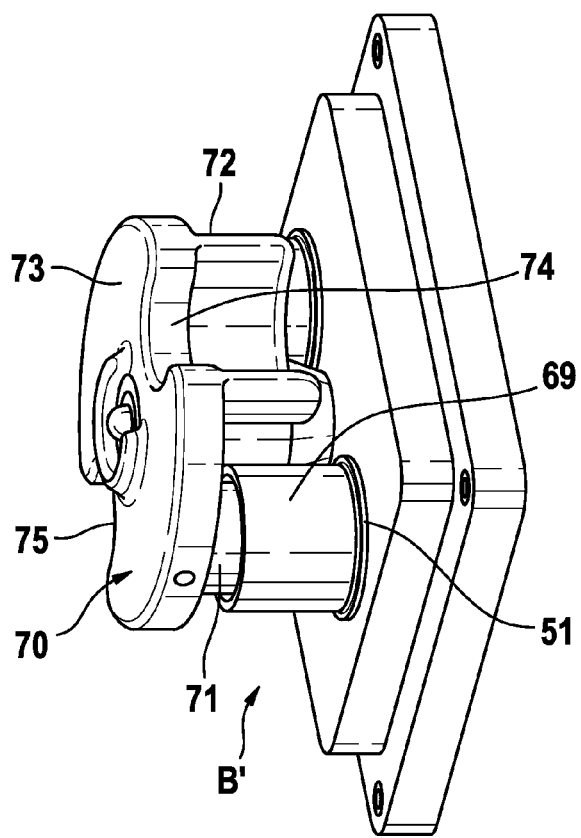
FIG. 8B shows the socket unit shown in FIG. 7 during the flushing process.

The alternative exemplary embodiment B' of the socket unit has a means 70 for closing off the two connecting pieces 65, 66, or for making a flow-permitting connection between the two connecting pieces 65, 66 to enable a flushing process to be carried out with a flushing solution (FIG. 7; FIG. 8A and FIG. 8B). The means 70 has two connectors 71, 72 which are arranged at the same distance from one another as the connectors 27, 28 of the plug unit A and which are of the same form as the connectors of the plug unit. The two connectors 71, 72 are closed off at a rear end in a flushing piece 73 or are connected to make a flow-permitting connection in the flushing piece 73.

The flushing piece 73 has semi-circular indentations 74, 75 on the two opposite sides on which the connectors 71, 72 are not arranged. The flushing piece 73 having the connectors 71, 72 is connected to the front portion 60 of the receiving piece 57 of the socket unit B'. For this purpose, the flushing piece 73 has a central opening 78 through which the front portion 60 of the receiving piece 57 extends (FIG. 9). Because the receiving piece 57 is mounted to be rotatable on the longitudinal axis 58, the flushing piece 73 too and the connectors 71, 72 can be rotated on the longitudinal axis 58 by the drive unit (not shown). FIG. 7 shows the short-circuiting piece 73 having the connectors 71, 72 in the position in which the plug unit A can be fitted onto the socket unit B'. In this position, the semi-circular indentations 74, 75 are situated in front of the connecting pieces 65, 66 of the socket unit B', while the connectors 71, 72 are positioned in a plane which is perpendicular to the plane in which the connecting pieces 65, 66 are positioned.

To initiate the flushing process, the flushing piece 73 having the connectors 71, 72 is pivoted through 90° as a result of the receiving piece 57 being rotated by the drive unit (not shown), and the connectors 71, 72 are thus situated in front of the connecting pieces 65, 66. However, this means that the connecting pieces are not yet closed off or that a flow-permitting connection has not yet been made between the connecting pieces (FIG. 8A). The connecting part 69 having the connecting pieces 65, 66 is then advanced out of the housing body 51 and the connectors 65, 66 are thus forced into the membranes of the connectors 71, 72. This makes a fluid-tight connection between the connecting pieces 65, 66 of the socket unit B' and the connectors 71, 72 and the two connecting pieces 65, 66 are thus closed off or short-circuited by means of the flushing piece 73 (FIG. 8B). On completion of the flushing process, the connecting pieces 65, 66 are retracted again and the flushing piece 73 having the connectors 71, 72 is rotated back to the starting position (FIG. 7).

The particular design of the means 70 for closing off or for making the flow-permitting connection forms part of the socket unit B'. There is no need for a separate plug or the like. The socket unit B' allows fully automatic control both of the connection of the plug unit A to the socket unit B' and of the initiation of the flushing process, thus simplifying the handling process as a whole. Because the insertion of the plug unit in the socket unit is detected, the filling process or emptying process can be initiated automatically. After the filling or emptying, the plug unit can be released automatically. The same is true of the flushing process. When the device 1 for supplying dialysis fluid is connected to the dialysis apparatus 2, the filling of the fluid reservoir 10 can also be started automatically by the insertion of the plug unit A in the socket unit B of the dialysis apparatus.

What is claimed is:

1. A medical apparatus, comprising:
    a socket unit for connection of a plug unit belonging to a device for supplying medical fluids, the socket unit including at least one connecting piece for connecting at least one connector of the plug unit, thus enabling a flow-permitting connection to allow fresh treatment fluid to be fed in or used treatment fluid to be fed out to be made when the connector is connected to the connecting piece;
    wherein the socket unit includes a receiving piece and a drive unit for moving the at least one connecting piece of the socket unit or the at least one connector of the plug unit; the socket unit includes the receiving piece and a locking body for connecting the plug unit and the socket unit such that the plug unit and socket unit are connected together when a relative movement occurs between the at least one connecting piece of the socket unit and the at least one connector of the plug unit; and
    wherein the locking body is configured to be introduced into a projecting piece of the plug unit, thus enabling the projecting piece of the plug unit to be splayed apart to make the connection between the plug unit and the socket unit.

2. The medical apparatus according to claim 1, wherein the receiving piece and the drive unit for moving the at least one connecting piece of the socket unit or the at least one connector of the plug unit, and the receiving piece and the locking body for connecting the plug unit and the socket unit cooperate such that the connection of the plug unit and socket unit takes place simultaneously with occurrence of the relative movement between the at least one connecting piece of the socket unit and the at least one connector of the plug unit.

3. The medical apparatus according to claim 1, wherein the at least one connecting piece of the socket unit is arranged to be immovable on the socket unit, the receiving piece and the drive unit for moving the at least one connecting piece of the socket unit or the at least one connector of the plug unit being configured such that the plug unit can be moved towards the socket unit or away from the socket unit.

4. The medical apparatus according to claim 1, wherein the receiving piece is movable in a longitudinal direction for receiving a projecting piece of the plug unit.

5. The medical apparatus according to claim 4, wherein the drive unit is configured for moving the receiving piece.

6. The medical apparatus according to claim 4, wherein the receiving piece of the socket unit takes a form of a tubular body displaceable in the longitudinal direction in which the projecting piece of the plug unit can be inserted.

7. The medical apparatus according to claim 4, wherein the receiving piece of the socket unit includes recesses to receive latching noses on the projecting piece of the plug unit.

8. The medical apparatus according to claim 1, wherein the locking body is arranged to be immobile in the socket unit.

9. The medical apparatus according to claim 8, wherein the locking body is arranged in the receiving piece.

10. The medical apparatus according to claim 4, further comprising:
    a sensing member for detecting the projecting piece of the plug unit in the receiving piece of the socket unit.

11. The medical apparatus according to claim 10, wherein the sensing member is resiliently pre-loaded and is so arranged in the socket unit that, when the projecting piece of the plug unit is introduced into the receiving piece of the socket unit, the sensing member is displaceable in opposition to the resilient pre-loading.

12. The medical apparatus according to claim 11, wherein the sensing member takes a form of a tubular body.

13. The medical apparatus according to claim 12, wherein the receiving piece, the sensing member and the locking body are concentrically arranged.

14. The medical apparatus according to claim 1, wherein the socket unit includes a first connecting piece for connection to a first connector of the plug unit and a second connecting piece for connection to a second connector of the plug unit, thus enabling a first flow-permitting connection to be made for feeding in fresh treatment fluid and a second flow-permitting connection to be made for feeding out used treatment fluid.

15. The medical apparatus according to claim 1, wherein the medical apparatus is one of a blood treatment apparatus, an extra-corporeal dialysis apparatus or an apparatus for peritoneal dialysis.

16. The medical apparatus according to claim 1, wherein the medical apparatus is one of an apparatus for filling the device for supplying medical fluids for a blood treatment apparatus, an extra-corporeal dialysis apparatus or an apparatus for peritoneal dialysis.

* * * * *